(12) United States Patent
Currie et al.

(10) Patent No.: US 7,390,796 B2
(45) Date of Patent: Jun. 24, 2008

(54) FATTY ACID MODIFIED FORMS OF GLUCOCORTICOIDS

(75) Inventors: Mark G. Currie, Sterling, MA (US); Steven Jones, Milford, MA (US); Charles M. Zepp, Hardwick, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 11/599,124

(22) Filed: Nov. 14, 2006

(65) Prior Publication Data

US 2007/0060555 A1 Mar. 15, 2007

Related U.S. Application Data

(63) Continuation of application No. 10/681,614, filed on Oct. 8, 2003, now abandoned.

(60) Provisional application No. 60/416,840, filed on Oct. 8, 2002.

(51) Int. Cl.
*A61K 31/56* (2006.01)
*C07J 5/00* (2006.01)

(52) U.S. Cl. .................. 514/179; 514/180; 514/826; 514/886; 552/566; 552/574; 552/576

(58) Field of Classification Search ................ 552/566, 552/574, 576; 514/179, 180
See application file for complete search history.

(56) References Cited

U.S. PATENT DOCUMENTS

| | | | | |
|---|---|---|---|---|
| 3,079,384 A | * | 2/1963 | Principe et al. ............... 435/53 |
| 3,929,768 A | | 12/1975 | Brattsand et al. ........ 260/239.55 |
| 4,693,999 A | * | 9/1987 | Axelsson et al. .............. 514/174 |
| 5,283,268 A | * | 2/1994 | Johnson et al. .............. 514/357 |
| 5,482,934 A | | 1/1996 | Calatayud et al. ........... 514/174 |
| 5,614,514 A | | 3/1997 | Axelsson et al. ............. 514/174 |
| 5,795,909 A | | 8/1998 | Shashoua et al. ........... 514/449 |
| 5,888,995 A | * | 3/1999 | Axelsson et al. ............. 514/174 |
| 6,120,752 A | | 9/2000 | Oliver et al. ................... 424/45 |
| 6,166,089 A | | 12/2000 | Kozak ......................... 514/642 |
| 6,264,923 B1 | | 7/2001 | Oliver et al. ................... 424/45 |
| 7,012,091 B1 | * | 3/2006 | Zamoyski .................... 514/450 |

FOREIGN PATENT DOCUMENTS

| | | |
|---|---|---|
| EP | 0164 636 | 5/1985 |
| EP | 0262 108 | 9/1987 |
| GB | 1269291 | 4/1970 |
| GB | 1292785 | 10/1972 |
| JP | 7277987 | * 10/1995 |
| WO | WO 92/13873 | 1/1992 |
| WO | WO 98/09982 | 3/1998 |
| WO | WO 98/32718 | 7/1998 |
| WO | WO 03/070745 | 2/2003 |

* cited by examiner

*Primary Examiner*—Barbara P. Badio
(74) *Attorney, Agent, or Firm*—Heslin Rothenberg Farley & Mesiti P.C.

(57) ABSTRACT

Compounds are disclosed of the formula

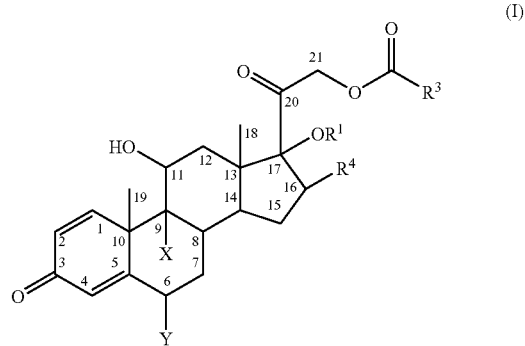

(I)

in which $R^3$ is $C_8$ to $C_{24}$ hydrocarbon or the residue of misoprostol. The compounds are useful for treating rhinitis and asthma, particularly by inhalation, and for treating inflammation, particularly by local or topical administration.

16 Claims, No Drawings

FATTY ACID MODIFIED FORMS OF GLUCOCORTICOIDS

CROSS REFERENCE TO RELATED APPLICATIONS

This application is a continuation of U.S. application Ser. No. 10/681,614, filed Oct. 8, 2003, now abandoned, which claims priority from US provisional application 60/416,840, filed Oct. 8, 2002, the entire disclosure of which are incorporated herein by reference.

FIELD OF THE INVENTION

The invention relates to antiasthmatic ester derivatives of glucocorticoids.

BACKGROUND OF THE INVENTION

Glucocorticoids, in topical, oral and inhaled formulations, are useful for their anti-inflammatory and immunosuppressive activities. Notwithstanding the sophistication of many formulations, many glucocorticoids exhibit significant side-effects that prevent realization of their maximum pharmacologic value. These side-effects stem, in part, from the difficulty of effectively delivering the glucocorticoid drug to a target tissue without increasing systemic concentrations of the drug.

Inhaled glucocorticoids are an effective therapy for the control of asthma, and improvement with steroids is one of the hallmarks of asthma [Barnes, P J (1998) in *Asthma: Basic Mechanisms and Clinical Management* ($3^{rd}$ ed)]. The inhaled glucocorticoids work to reduce the inflammation in either lungs, e.g. for asthma, or nose, e.g. for nasal allergies. Inhaled glucocorticoids are most often administered using a metered dose inhaler (MDI). In the best of circumstances, in controlled clinical settings, only around 30% of the administered dose gets into the lungs. In the general patient population probably only 10% or so of the dose gets into the lungs due to improper use of the inhaler. The rest of the administered drug is deposited in the throat and upper airways, or is swallowed. The drug that is deposited in the throat is responsible for some side effects seen with inhaled glucocorticoids (cough, oropharyngeal candidiasis and dysphonia). For early generation inhaled glucocorticoids, the swallowed drug leads to the same side effects seen with oral glucocorticoids. In light of the tremendous efficacy of inhaled glucocorticoids in asthma, much effort has gone into reducing the side effects from their use. Although newer glucocorticoids (e.g. budesonide, ciclesonide, triamcinolone and fluticasone) exhibit reduced systemic side effects from swallowed drug—being either poorly absorbed in the gut or subject to extensive inactivation in the liver—they nonetheless display systemic side effects as a result of absorption from the lung into the systemic circulation. The side effects include decreased bone density (Israel, E et al., (2001), *New England Journal of Medicine* 345:941-947 and Wong, C A et al., (2000) *Lancet* 355:1399-1403), which has been correlated with increased risk of fracture. Thus the need still exists for inhaled glucocorticoids with reduced systemic effects.

Several approaches have been suggested to reduce systemic effects. One such approach takes advantage of inactive prodrugs that are activated in the lung tissues. For example, Dietzel et al. [*Prog. Respir Res*. 31, 91-93 (2001)] have described an isopropyl group esterified at the 21 position of the glucocorticoid core structure. Another approach that has been suggested is the formulation of a glucocorticoid as a liposome. Axelsson et al. in a series of U.S. patents (U.S. Pat. Nos. 4,693,999; 5,614,514 and 5,888,995) describe selected glucocorticoids modified for formulation into liposomes by esterification at the 21 position with saturated and mono-unsaturated fatty acids with chain lengths up to 20 carbons.

SUMMARY OF THE INVENTION

In one aspect, the invention relates to compounds of Formula I:

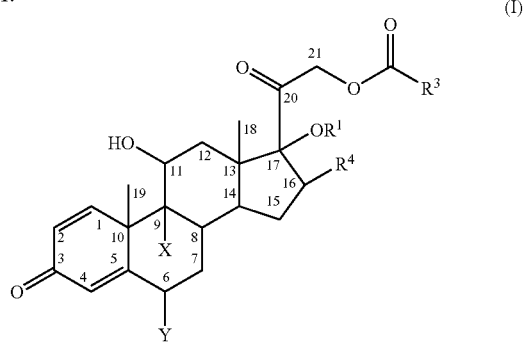

wherein
$R^1$ and $R^2$, independently for each occurrence, represent a hydrogen, lower alkyl or lower acyl, or taken together $R^1$ and $R^2$ form a substituted or unsubstituted ketal;
$R^3$ is chosen from saturated and unsaturated $C_8$ to $C_{24}$ hydrocarbon, and

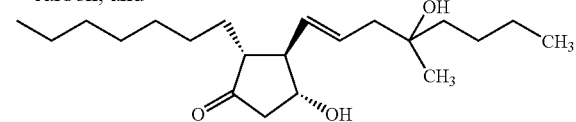

$R^4$ is methyl or —$OR^2$; and
X and Y are independently hydrogen or halogen.

In another aspect the invention relates to methods for treating bronchospasm, for inducing bronchodilation and for treating rhinitis, asthma, chronic obstructive pulmonary disease (COPD) and inflammatory diseases and conditions comprising administering the compounds of formula I.

In another aspect, the invention relates to pharmaceutical formulations for inhalation comprising the compounds of formula I, a pharmaceutically acceptable fluid for suspension or solution, and, for metered dose inhalers, additionally comprising a propellant.

DETAILED DESCRIPTION OF THE INVENTION

The invention relates to compounds of Formula I:

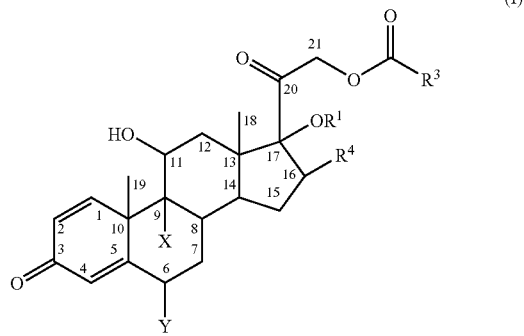

in which the substituents are as defined above. In preferred embodiments the steroid has the absolute stereochemistry shown:

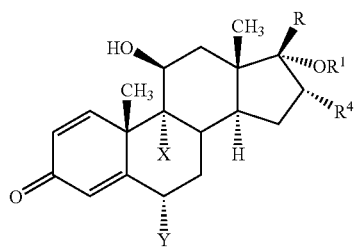

Examples of steroids having the foregoing structure include budesonide, ciclesonide, fluticasone and triamcinolone. Preferred embodiments include compounds in which the steroid nucleus is of formulae:

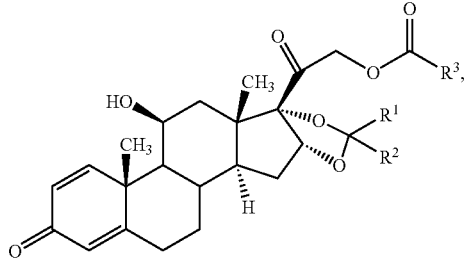

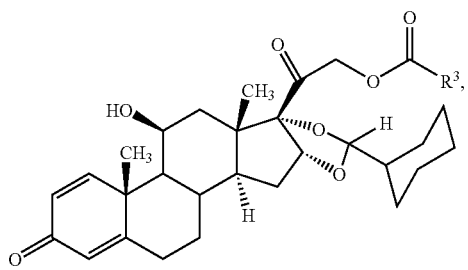

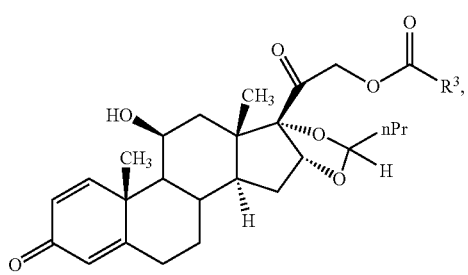

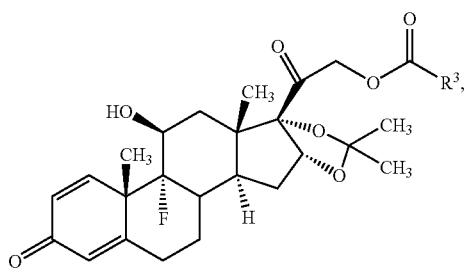

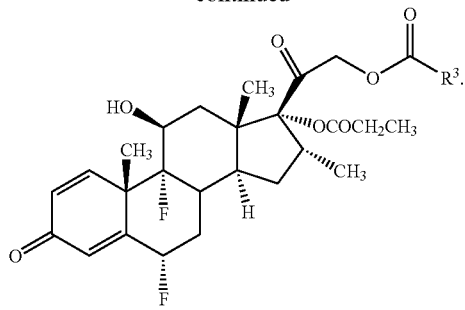

Preferred embodiments of $R^3$ are:
the residue of phytanic acid:

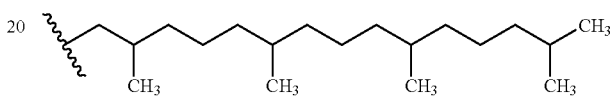

the residue of eicosapentaenoic acid (EPA):

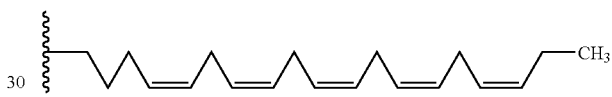

the residue of docosapentaenoic acid (DPA):

and
the residue of docosahexaenoic acid (DHA):

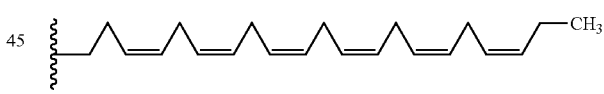

Alkyl is intended to include linear, branched, or cyclic hydrocarbon structures and combinations thereof. Preferred alkyl groups are those of $C_8$ to $C_{24}$. Cycloalkyl is a subset of alkyl and includes cyclic hydrocarbon groups, in this case preferably from 6 to 8 carbon atoms. Lower acyl is acyl of one to six carbons, e.g. acetyl, propionyl, isopropanoyl, butanoyl, sec-butanoyl, valeroyl, and hexanoyl.

$C_8$ to $C_{24}$ Hydrocarbon includes alkyl, cycloalkyl, alkenyl, alkynyl, aryl and combinations thereof. Examples include phenethyl, cyclohexylmethyl, camphoryl, naphthylethyl, DHA, EPA and DPA.

The compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as, their racemic and optically pure forms. Optically active isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

The abbreviations Me, Et, Ph, Tf, Ts and Ms represent methyl, ethyl, phenyl, trifluoromethanesulfonyl, toluensulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The term "a residue of [a named] acid" when used, for example, to describe $R^3$, refers to a carboxylic acid minus the elements that are considered part of the base Markush structure. For example, in the molecule illustrated below:

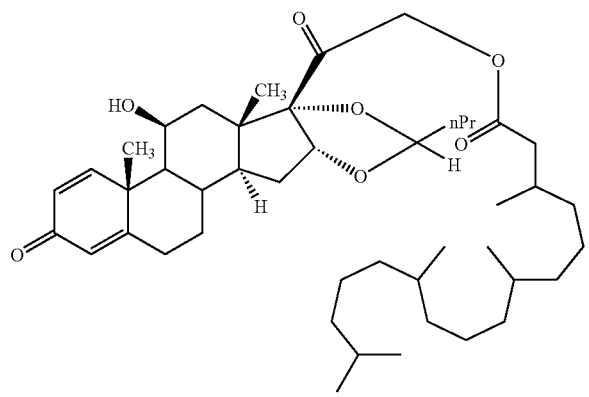

after one subtracts the carboxylate linkage —OCO— that constitutes part of the base Markush structure, the portion of the carboxylic acid (phytanic acid) that remains is:

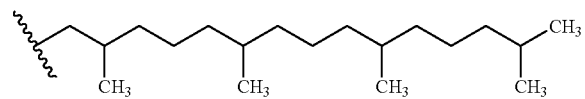

This and similar structures of fatty acids that lack the carboxyl at the point of attachment are referred to herein as "residues of acids".

The term "methods of treating" when used in connection with the present invention means amelioration, prevention or relief from the symptoms and/or effects associated with asthma and rhinitis. The person of ordinary skill in the medical art recognizes that "prevention" of the symptoms and/or effects associated with asthma and rhinitis is not an absolute term. In the medical art it is understood to refer to the prophylactic administration of a drug to substantially diminish the likelihood or seriousness of the condition.

The compounds of the invention are useful for treating COPD, asthma and rhinitis. They are also useful for intra-articular injection for alleviating the joint pain, swelling and stiffness associated with rheumatoid arthritis and osteoarthritis with an inflammatory component; also for bursitis, epicondylitis and tenosynovitis. They may be used topically, transdermally and intradermally (intra-lesional) in lichen simplex chronicus, granuloma annulare, lichen planus, keloids, alopecia areata, discoid lupus erythematosus, localised neurodermatitis, cystic acne, granuloma annulare, nummular and dyshydrotic eczema, and hypertrophic scars (keloids). The treatment of macular degeneration with compounds of the invention is analogous to that described in Billson, U.S. Pat. No. 5,770,589, which is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Exemplary syntheses of budesonide esters are described below. One skilled in the art will recognize that the syntheses can be adapted to prepare a variety of esters of budesonide, ciclesonide, fluticasone or triamcinolone.

EXAMPLES

Example 1

Synthesis of the docosahexaenoic acid ester of budesonide

A solution of 1.0 gm ($3\times10^{-3}$ moles) of docosahexaenoic acid in methylene chloride (10 mL) was treated with thionyl chloride (0.357 gm, $3\times10^{-3}$ moles) and two drops of DMF. This solution was heated at 30° C. for two hours. After cooling the solvent and any unreacted thionyl chloride were removed under vacuum. The residue was added dropwise to a solution of budesonide (1.0 gm, $2.3\times10^{-3}$ moles) in pyridine (10 mL) with stirring and ice cooling. After the addition was complete the reaction mixture was stirred at room temperature for one hour. Water (50 mL) containing 85% phosphoric acid (5 mL) was added and the insoluble material was extracted into diethyl ether (50 mL). After discarding the aqueous phase, the ether solution was washed with water (50 mL) containing 85% phosphoric acid (5 mL). The ether solution was dried over magnesium sulfate, then filtered and stripped under vacuum. The residue was purified by chromatography on silica using 50/50 hexane and ethyl acetate as eluent. The product was collected as it was eluted from the column and the pooled fractions were stripped under vacuum. The yield was 670 mg (39%).

Example 2

Synthesis of the docosapentaenoic acid ester of budesonide

A solution of 1.0 gm ($3\times10^{-3}$ moles) of docosapentaenoic acid in methylene chloride (10 mL) was treated with thionyl chloride (0.357 gm, $3\times10^{-3}$ moles) and two drops of DMF. This solution was heated at 30° C. for two hours. After cooling the solvent and any unreacted thionyl chloride were removed under vacuum. The residue was added dropwise to a solution of budesonide (1.0 gm, $2.3\times10^{-3}$ moles) in pyridine (10 mL) with stirring and ice cooling. After the addition was complete the reaction mixture was stirred at room temperature for one hour. Water (50 mL) containing 85% phosphoric acid (5 mL) was added and the insoluble material was extracted into diethyl ether (50 mL). After discarding the aqueous phase, the ether solution was washed with water (50 mL) containing 85% phosphoric acid (5 mL). The ether solution was dried over magnesium sulfate, then filtered and stripped under vacuum. The residue was purified by chromatography on silica using 2/1 hexane and ethyl acetate as eluent. The product was collected as it was eluted from the column and the pooled fractions were stripped under vacuum. The yield was 885mg (52%).

Example 3

Synthesis of the eicosapentaenoic acid ester of budesonide

A solution of 0.90 gm ($3\times10^{-3}$ moles) of eicosapentaenoic acid in methylene chloride (10 mL) was treated with thionyl chloride (0.357 gm, $3\times10^{-3}$ moles) and two drops of DMF. This solution was heated at 30° C. for two hours. After cooling the solvent and any unreacted thionyl chloride were removed under vacuum. The residue was added dropwise to a solution of budesonide (1.0 gm, $2.3\times10^{-3}$ moles) in pyridine (10 mL) with stirring and ice cooling. After the addition was complete the reaction mixture was stirred at room temperature for one hour. Water (50 mL) containing 85% phosphoric acid (5 mL) was added and the insoluble material was extracted into diethyl ether (50 mL). After discarding the aqueous phase, the ether solution was washed with water (50 mL) containing 85% phosphoric acid (5 mL). The ether solution was dried over magnesium sulfate, then filtered and stripped under vacuum. The residue was purified by chromatography on silica using 2/1 hexane and ethyl acetate as eluent. The product was collected as it was eluted from the column and the pooled fractions were stripped under vacuum. The yield was 750mg (35%).

Example 4

Synthesis of the phytanic acid ester of budesonide

The phytanic acid ester of budesonide was prepared in similar fashion to the procedure described for the previous examples from phytanic acid and budesonide.

Biological Testing

Nominal 5 mM solutions of the budesonide fatty acid esters were made in DMSO by adding the following amounts of compound and DMSO: docosahexaenoic acid ester of budesonide 7.5 mg in 2 ml DMSO, docosapentaenoic acid ester of budesonide 32.9 mg in 9.1 ml DMSO and eicosapentaenoic acid ester of budesonide 20.3 mg in 5.8 ml DMSO. A 5 mM solution of budesonide was made by dissolving 4.5 mg of budesonide (Sigma Chemical Company product number B 7777) in 2.1 ml DMSO.

The WI-38 human lung fibroblast line was obtained from the ATCC (catalog number 75-CCL) and maintained in Basel Medium Eagle with Earle's salts (GibcoBRL product number 21010-046) supplemented with 2 mM glutamine and 10% fetal calf serum at 37° C. in a 7% $CO_2$ (balance air), humidified atmosphere. One week before experiments were done, the WI-38 cells were seeded into 48-well tissue culture dishes and maintained in media containing 10% fetal calf serum. The cells were used when confluent. The day before the experiment the cells were fed fresh media containing 10% fetal calf serum (0.25 ml per well). One the day of the experiment the media was removed from the cells and 0.25 ml of media containing 5% fetal calf serum added.

The rat alveolar macrophage cell line RAW 264.7 was obtained from the ATCC (catalog number 71-TIB) and maintained in Dulbecco's Modified Eagle Medium (GibcoBRL product number 11960-044) supplemented with 2 mM glutamine, 1 mM sodium pyruvate and 10% fetal calf serum at 37° C. in a 10% $CO_2$ (balance air), humidified atmosphere.

One week before experiments were done, the WI-38 cells were seeded into 48-well tissue culture dishes and maintained in media containing 10% fetal calf serum. The cells were used when confluent. The day before the experiment the cells were fed fresh media containing 10% fetal calf serum (0.25 ml per well). One the day of the experiment the media was removed from the cells and 0.25 ml of media containing 5% fetal calf serum added.

To determine the $IC_{50}$ values for the compounds, 1 to 1000 dilutions were made of the 5 mM stock solutions in DMSO to give 5 uM solutions. These solutions were serially diluted 1:2 in DMSO to give a series of 12 dilutions ranging from 5 uM to 2.4 nM. 0.0025 ml aliquots of the 12 dilutions were added to wells of the WI-38 cells to give final compound concentrations ranging from 50 nM to 0.024 nM. The cells were stimulated by addition of 0.001 ml of 0.025 ug/ml recombinant human Interleukin-1β (IL-1β-Calbiochem catalog number 407615) in 0.1% bovine serum albumin in phosphate buffered saline. The cells were incubated for 24 hours and the supernatants harvested. The level of $PGE_2$ in the supernatants was assayed using a commercial Enzyme Immuno Assay (EIA) kit (Cayman Chemical catalog number 514010) after diluting 1:10 in EIA buffer according to the manufacturer's directions. The data from these experiments was fit to a 4 parameter logistic function using the $IC_{50}$ routine in the Grafit 4 program (Erithecus software).

$IC_{50}$ values determined in this manner were:

| | |
|---|---|
| Budesonide | 0.2 nM |
| Docosahexaenoic (DHA) acid ester of budesonide | 1.1 nM |
| Docosapentaenoic (DPA) acid ester of budesonide | 9.0 nM |
| Eicosapentaenoic (EPA) acid ester of budesonide | 1.3 nM |

To test for duration of action, a wash-out experiment was performed as follows. Confluent cells in 48-well tissue culture dishes were treated with concentrations of the above compounds that were 50 times the $IC_{50}$ values as determined above for 2 hours. The media was removed and the wells washed 5 times with 0.25 ml of media containing 5% fetal calf serum. 0.25 ml of media containing 5% fetal calf serum was then added. The WI-38 cells were stimulated by addition of 0.001 ml of 0.025 ug/ml recombinant human Interleukin-1β (Calbiochem catalog number 407615) in 0.1% bovine serum albumin in phosphate buffered saline. The RAW 264.7 cells were stimulated by addition of 0.001 ml of 0.5 ug/ml E. coli 0127:B8 lipopolysaccharide (LPS-Sigma catalog number L-4516) in 0.1% bovine serum albumin in phosphate buffered saline. The cells were incubated for 24 hours and the supernatants harvested. The level of $PGE_2$ in the supernatants was assayed using a commercial Enzyme Immuno Assay (EIA) kit (Cayman Chemical catalog number 514010) after diluting 1:10 in EIA buffer according to the manufacturer's directions. Eight wells were used for each concentration and the results from these eight wells were averaged.

The results were as follows: minimum values are for cells that did not receive any compounds or stimulant and maximum values were from cells that did not receive any compounds but were stimulated with either IL-1β or E. coli LPS.

| | $PGE_2$ production (pg/ml) | |
|---|---|---|
| Treatment | WI-38 cells | RAW 264.7 cells |
| Minimum | 312 | 284 |
| Budesonide | 2688 | 1339 |

-continued

| Treatment | PGE$_2$ production (pg/ml) | |
| --- | --- | --- |
| | WI-38 cells | RAW 264.7 cells |
| Docosahexaenoic acid ester of budesonide | 2075 | 892 |
| Docosapentaenoic acid ester of budesonide | 200 | 622 |
| Eicosapentaenoic acid ester of budesonide | 806 | 576 |
| Maximum | 7788 | 2965 |

Putative anti-inflammatory agents may also be tested in vivo in a rat paw edema model [Hirschelmann, R. and Bekemeier, H., Int J Tissue React 6, 471-475 (1984)], which persons of skill in the art accept as predictive of efficacy in treating asthma and rhinitis in humans. The phytanic acid ester of budesonide was tested in this model. The results shown below demonstrate a greatly extended duration of effect which allows once-a-day dosing.

| | percent reduction in paw volume | | | | | |
| --- | --- | --- | --- | --- | --- | --- |
| dose µg/paw | 1.5 hours | 3 hours | 4.5 hours | 24 hours | 48 hours | 72 hours |
| Budesonide | | | | | | |
| 0.001 | 0 | 20 | 15 | 4 | 3 | 0 |
| 0.01 | 0 | 18 | 0 | 11 | 0 | 3 |
| 0.1 | 14 | 5 | 0 | 0 | 0 | 0 |
| 1 | 36 | 45 | 32 | 44 | 17 | 10 |
| 10 | 11 | 33 | 34 | 70 | 38 | 6 |
| Phytanic acid ester of Budesonide | | | | | | |
| 0.0017 | 0 | 10 | 12 | 4 | 7 | 3 |
| 0.017 | 0 | 0 | 0 | 0 | 0 | 6 |
| 0.17 | 0 | 0 | 0 | 0 | 0 | 0 |
| 1.7 | 18 | 15 | 2 | 30 | 17 | 16 |
| 17 | 11 | 5 | 2 | 74 | 79 | 65 |

For administration to treat asthma, rhinitis, COPD and respiratory conditions, the drug is suitably inhaled from a nebulizer, from a pressurized metered dose inhaler or as a dry powder from a dry powder inhaler (e.g. sold as TURBUHALER®) or from a dry powder inhaler utilizing gelatin, plastic or other capsules, cartridges or blister packs.

A diluent or carrier, generally non-toxic and chemically inert to the medicament, e.g. lactose, dextran, mannitol or glucose or any additives that will give the medicament a desired taste, can be added to the powdered medicament.

Formulations and devices for nebulizers, metered dose inhalers and dry powder inhalers are well known to those skilled in the art. In formulations where the active ingredient is in a suspension it is important that the particles are below 20 µm in size and preferably below 5 µm in size. This may be achieved by micronization, crystallization, spray drying or other known techniques.

The solvent or suspension agent utilized for nebulization may be any pharmacologically suitable fluid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both inorganic salts, such as alkali metal or ammonium halogen salts e.g. sodium chloride, potassium chloride or organic salts, such as potassium, sodium and ammonium salts of organic acids, e.g., ascorbic acid, citric acid, acetic acid, tartaric acid, etc. may be used for this purpose.

Other excipients and additives may be added to the formulation. The active ingredient may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid etc.; a complexing agent such as EDTA or citric acid and salts thereof; or an antioxidant such as vitamin E or ascorbic acid. These may be used alone or together to stabilize the active ingredient. Preservatives can also be added such as benzalkonium chloride or benzoic acid and salts thereof. Surfactant may be added particularly to improve the physical stability of suspensions. These include lecithins, disodium dioctylsulphosuccinate, oleic acid and sorbitan esters.

The active ingredient may also be suspended or dissolved in a liquified propellant, sealed in a container with a metering valve and fitted into an actuator. Such metered dose inhalers are well known in the art. The metering valve may meter 10 to 500 µL and preferably 25 to 150 µL.

The propellants used may be halocarbons, hydrocarbons or other liquified gasses. The most frequently used are trichlorofluoromethane (propellant 11), dichlorfluoromethane (propellant 12), dichlortetrafluoroethane (propellant 114), tetrafluoroethane (HFA-134a), 1,1-difluoroethane (HFA-152a), difluoromethane (HFA-32), pentafluoroethane (HFA-125), heptafluoropropane (HFA-227ea), perfluoropropane, perfluorobutane, perfluorpentane, butane, isobutane, and pentane. In particular, tetrafluoroethane (HFA-134a) and heptafluoropropane (HFA-227ea) and mixtures thereof are used.

As well as propellant, formulations may contain other excipients. Surfactant may be added particularly to improve the physical stability of suspensions and valve performance. These include lecithins, disodium dioctylsulphosuccinate, oleic acid and sorbitan esters. Cosolvents may also be added to improve solubility of surfactant in propellant or modify the pharmacological performance. These include alcohols and glycols, e.g., ethanol, isopropylalcohol, glycerol, propylene glycol, polyethylene glycol, etc., or mixtures thereof. Further excipients may be added to improve performance or taste, e.g., fatty acids and salts thereof such as magnesium stearate, menthol oil etc.

Dry powder inhalers include devices which meter drug from a chamber within the device or those that deliver pre-metered doses utilizing gelatin, plastic or other capsules, cartridges, or blister packs and/or strips.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The topical pharmaceutical carrier may include any substance capable of dispersing and maintaining contact between the active ingredients and the skin. The vehicle may be glycerin, alcohol or water based. Examples of such vehicles include aloe vera, which is a gel base, together with ethanol, isopropyl alcohol, water, propylene glycol and a non-ionic surfactant such as laureth-4. Other water-based alcohol/glycerin vehicles and carriers are within the scope of the present invention. A typical water-based lotion will contain from 45 to 50 parts of glycerin, one to three parts Tween 80TM, from 45 to 50 parts of water and from 1 to 50 parts of the compound of the invention.

Also included in the scope of the invention are ointments, emulsions or dispersions in which water, if present, is a minor constituent. Typical ointment formulation comprises from 90 to 98 parts of a mixture of petrolatum, mineral oil, mineral wax and wool wax alcohol, from 0.5 to 3 parts of a mixture of polyoxyethylene and sorbitan monooleate (Tween 80TM), from 1 to 5 parts of water, and from 1 to 50 parts of the compound of the invention. Another suitable non-aqueous ointment can be prepared from 95 parts of liquid petrolatum USP, 5 parts polyethylene and from 1 to 50 parts of the compound of the invention. The resulting ointment spreads easily and has an even consistency over wide temperature extremes. It is, in addition, non-irritating and non-sensitizing.

Formulations of the compounds of the invention may also be prepared containing from 0 to 25% by weight of urea. In general, in such urea containing ointments, the water content will vary from 5 to 50% by weight of the composition. Any suitable ointment carrier may be used such as lanolin, ethylene glycol polymers and the like. In the case of formulations containing urea, it is known in the art that borate salts may often be added to stabilize the pharmaceutical composition (see U.S. Pat. No. 2,917,433, the disclosure of which is incorporated herein by reference).

Water based compositions may also be employed, in which case the compound of the invention will commonly be in solution, and the aqueous solution may, if desired, be thickened with a suitable gel to provide a less mobile composition. Such compositions are well known in the art.

What is claimed is:

1. A compound of Formula I:

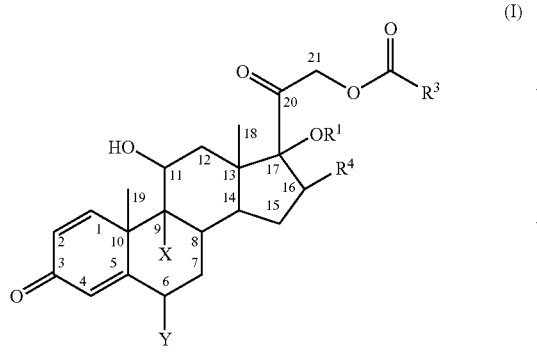

wherein
R$^1$ and R$^2$, independently for each occurrence, represent a hydrogen, lower alkyl or lower acyl, or taken together R$^1$ and R$^2$ form a substituted or unsubstituted ketal;
R$^3$ is

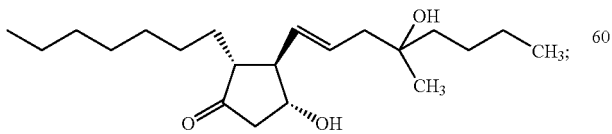

R$^4$ is methyl or —OR$^2$; and
X and Y are independently hydrogen or halogen.

2. A compound according to claim 1 of formula:

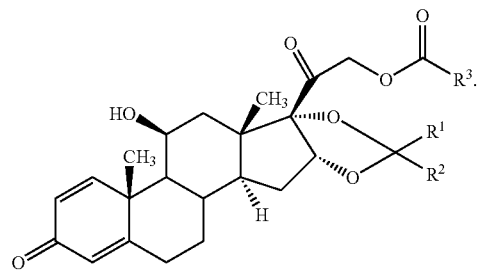

3. A compound according to claim 2 of formula:

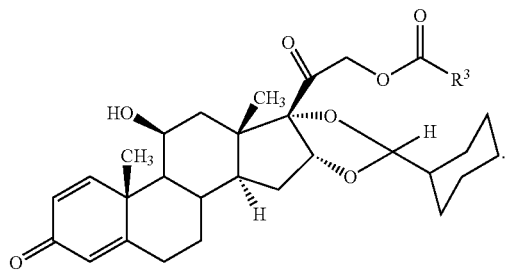

4. A compound according to claim 2 of formula

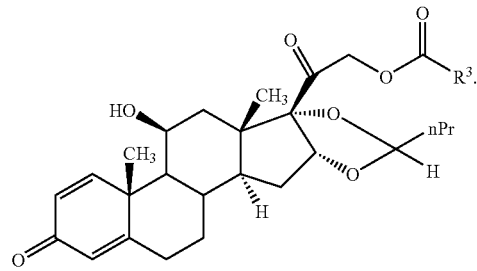

5. A compound according to claim 2 of formula

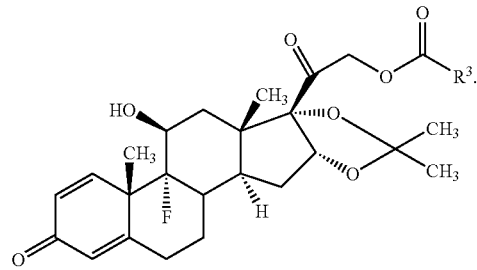

6. A compound according to claim 1 of formula:

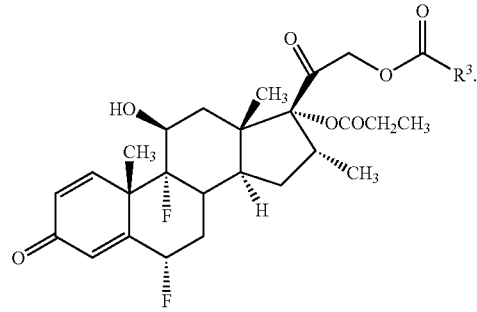

7. A compound of formula

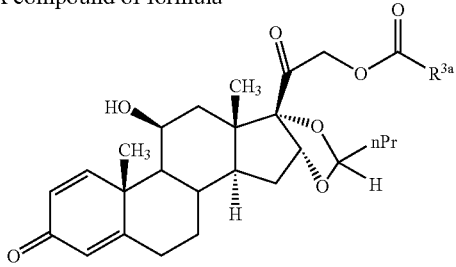

wherein $R^{3a}$ is chosen from the residue of docosapentaenoic acid:

and the residue of docosahexaenoic acid:

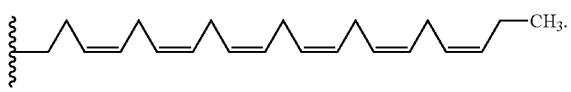

8. A pharmaceutical formulation for inhalation comprising a compound according to claim 1 and a pharmaceutically acceptable fluid for solution or suspension.

9. A pharmaceutical formulation according to claim 8 additionally comprising a propellant.

10. A method for treating bronchospasm comprising administering a compound of claim 1.

11. A method for inducing bronchodilation comprising administering a compound of claim 1.

12. A method for treating inflammatory conditions comprising administering a compound of claim 1.

13. A method according to claim 12 wherein said inflammatory condition is chronic obstructive pulmonary disease.

14. A method according to claim 12 wherein said inflammatory condition is asthma.

15. A method according to claim 12 wherein said inflammatory condition is rhinitis.

16. A method according to claim 12 wherein said compound is administered by inhalation.

* * * * *